United States Patent
Tsoukalis (10) Patent No.: US 8,551,038 B2
(45) Date of Patent: Oct. 8, 2013

(54) PUMP INFUSION SYSTEM

(75) Inventor: Achilleas Tsoukalis, Pallini (GR)

(73) Assignee: Micrel Medical Devices S.A., Pallini (GR)

( * ) Notice: Subject to any disclaimer, the term of this patent is extended or adjusted under 35 U.S.C. 154(b) by 0 days.

(21) Appl. No.: 13/185,990

(22) Filed: Jul. 19, 2011

(65) Prior Publication Data

US 2012/0016295 A1 Jan. 19, 2012

(30) Foreign Application Priority Data

Jul. 19, 2010 (GR) .................................. 100100392

(51) Int. Cl.
*A61M 31/00* (2006.01)
(52) U.S. Cl.
USPC ........................................................... 604/66
(58) Field of Classification Search
USPC ........................................................... 604/66
See application file for complete search history.

(56) References Cited

U.S. PATENT DOCUMENTS

| | | | |
|---|---|---|---|
| 4,857,713 A | 8/1989 | Brown | |
| 4,875,713 A * | 10/1989 | Carstensen | 285/55 |
| 5,317,506 A * | 5/1994 | Coutre et al. | 604/65 |
| 6,985,870 B2 * | 1/2006 | Martucci et al. | 705/3 |
| 7,384,410 B2 * | 6/2008 | Eggers et al. | 604/67 |
| 7,506,807 B2 * | 3/2009 | Durrell et al. | 235/382 |
| 7,751,907 B2 * | 7/2010 | Blomquist | 700/17 |
| 2004/0225252 A1 * | 11/2004 | Gillespie et al. | 604/19 |
| 2008/0294294 A1 * | 11/2008 | Blomquist | 700/282 |
| 2009/0112333 A1 * | 4/2009 | Sahai | 700/3 |

* cited by examiner

*Primary Examiner* — Aarti B Berdichevsky
(74) *Attorney, Agent, or Firm* — Merek, Blackmon & Voorhees, LLC (57) ABSTRACT

In a pump infusion system comprising a pump adapted to be attached to a user and to cause infusion of pharmaceutical substances into the user's body, questions regarding the effects of administration of the pharmaceutical substances are provided, answers to said questions are transmitted to an attending staff, said answers are recorded, and said pump is controlled so as to adjust the dose of the pharmaceutical substances in accordance with said answers. Further, for a safe remote programming of such a pump infusion system, a predetermined program is assigned, a protocol to be programmed is compared with a protocol coming from the pump, possible errors of non-medically certified intervening devices and means are eliminated, and the programming is executed.

17 Claims, 3 Drawing Sheets

PUMP INFUSION SYSTEM

CROSS-REFERENCE TO RELATED APPLICATION

The present application claims the priority under 35 U.S.C. 119 of Greek Application No. GR 2010 0100392, filed Jul. 19, 2010.

The present invention relates to a pump infusion system comprising a pump adapted to be attached to a user and to cause infusion of pharmaceutical substances into the user's body. Further, the present invention relates to a method for remote programming such a pump infusion system.

In medical practice, pumps for infusion of analgesics for the limitation or reduction of post-operative pain (regional analgesia) or of chronic pain (intravenous or general analgesia) are known. Usually, such pumps are adapted to provide a basic continuous infusion of a drug with a certain dose on demand, when the user or patient presses a button connected to the pump by a cable, so that such a system or measure acts somewhat like a pain feedback. Therefore, such pumps are called PCA (Patient Controlled Analgesia) or PCEA (Patient Controlled Epidural Analgesia) pumps, i.e. pumps wherein analgesia is regulated by the user or patient himself/herself.

Today's practice is to infuse pharmaceutical substances on drugs unattended, based on an early clinical study specifying a 'blind' prescription rule. Further, when the physician programs the pump, there are limits, such as the time which intervenes between doses and the volume of the total dose allowed on demand.

For providing local analgesia, the catheter is placed near the nerve which carries the topical pain to the brain, and for better medical results e.g. in case of an operation of a limb the user or patient is asked to exercise the operated limb despite of the pain. Hence, there is a need for limitation or reduction of the local pain and for control of mobility of an operated limb which is blocked by analgesic drugs. Analgesia should occur within a range between the limits where the patient is in pain at the one end and where blockage of movement is caused due to an extreme dose of analgesic drugs at the other end. Despite of increased efforts for safe measurement of infusion results, the therapeutic effects and side effects, there are many medical indications which are not easy to measure, such as pain, dizziness, inclination for vomit etc., wherein the participation of the patient to express how she/he feels is critical and important and is used in all clinical trials of drugs today. The user's or patient's participation in the description of therapy results is important also for the assessment of the total therapy, side effects, attendants and services.

In medical practice, nurses record every patient's pain level on pieces of paper. However, the frequency of recording on-demand dose button pressing (bolus) and the doses which are usually recorded and depicted by conventional pain pumps is not satisfying for the clinical presentation. Therefore, there is a need for the user's or patient's participation in the description of therapy results.

U.S. Pat. No. 6,985,870 A and U.S. Pat. No. 4,857,713 A each deal with techniques of safe infusion with infusion identification and the physician's prescription. U.S. Pat. No. 7,506,807 A, U.S. Pat. No. 7,384,410 A, and U.S. Pat. No. 5,317,506 A each deal with the management and automization of hospital care including drug infusion.

It is an object of the present invention to provide an improved telemedicine system with the use of information-assessment of the therapy by the user or patient herself/himself.

It is a further object of the present invention to provide a system of safe infusion including a pump with the possibility of therapy feedback, with the participation of the user or patient herself/himself and the possibility of remote monitoring and correction of the therapy from the attending staff.

It is a still further object of the present invention to provide for a safe remote programming of the aforementioned system.

In order to achieve the above and further objects, according to a first aspect of the present invention there is provided a pump infusion system comprising a pump adapted to be attached to a user and to cause infusion of pharmaceutical substances into the user's body, characterized by questions-providing means for providing questions regarding the effects of administration of the pharmaceutical substances, transmitting means for transmitting answers to said questions to an attending staff, recording means for recording said answers, and control means for controlling said pump so as to adjust the dose of the pharmaceutical substances in accordance with at least one of said answers.

Accordingly, the present invention proposes an improved technique for treatment of therapies, such as regional anesthesia, using feedback for describing in detail the clinical image of the user or patient, their recording and imaging, their transmission to a remote location for storage and for briefing the attending physicians and other staff, and the local or remote regulation of the dosing of the pharmaceutical substances by the pump which is, thus, triggered by at least one of the answers so as to adjust the dosing of the pharmaceutical substances accordingly. The present invention provides for safe and effective means of communication with the user or patient for determination and improvement of therapy effectiveness. Therefore, due to the present invention, e.g. a better mobility of an operated limb of the user or patient is achieved with minimal pain. However, the present invention is not limited to the treatment of pain only; rather, the present invention can be applied to other diseases as well which require infusion, such as Parkinson (apomorphine infusion), pulmonary hypertension (Flolan infusion) etc., wherein the feedback measurement of therapy effectiveness can be different in each case. E.g. in case of using an accelerometer measuring tremor with Parkinson, questions regarding analgesia which is hard to measure and regarding tremor-stillness which is not easily recognizable by said accelerometer are to be provided to the user or patient.

Due to the solution of the present invention, a real time reported feedback on therapy results or side effects is realized, so that e.g. casualties caused by medication error can be prevented, side effects being a borderline for the drug can be prevented by reducing or stopping infusion before the side effects become dangerous, the toxic limit for the patient's genotype can be considered, and drugs having metabolic effects depending on living conditions (like insulin) can be safely administered.

So, the present invention allows the user to prompt through the pump infusion system and to give feedback about therapeutic results or side effects from the pharmaceutical substance infused, about the assessment of the therapeutic service etc., resulting in a more effective therapy and its correction. Further, the present invention allows for an automatic notification, preferably via the internet, or a notification on demand e.g. by the insurance company which subsidizes the therapy.

After all, the present invention proposes a way to trial phases of a pharmaceutical substance or drug where its dose prescription depends on feedback reading, and not e.g. on the user's or patient's age and weight. This is achieved according to the present invention by providing remote answers from the user or patient to questions, which is very simple but results in big therapy advantages since most side effects like vomiting, nausea etc. cannot be measured by sensors.

According to a preferred embodiment, the questions-providing means is adapted to provide questions in predetermined time intervals which can be programmed. At predetermined time intervals which can be programmable, preferably, a series of questions is provided which describe quantitatively and qualitatively the condition of mobility, pain etc. According to the kind of list or table of questions appearing, the user or patient may answer either "yes" or "no" or with a quantitative reference, e.g. by selection from a list of prescribed types of answers given as e.g. "bad"-"good"-"better"-"excellent" or numbers from "1" to "10" or by using a level at a triangular proportionally increasing graphic scale like 'volume' controls. It is further an improvement over the prior art that a classic hand set provided as a so-called "bolus button" on PCA (Patient Control Analgesia) pumps can be modified so as to give a more comprehensive feedback about the therapy by using a level control like a linear potentiometer operating one-dimensionally or a joystick operating in two dimensions, wherein the meaning of each dimension is different in accordance with the therapy. This is like a trigger in case of the patient's distress when the patient does not feel good with a current therapy and therefore demands a correction process, in particular a correction of the dosage of the pharmaceutical substance infused, to be initiated with a first feedback indicating a "discomfort" level, wherein the system can ask him for more specific information needed immediately or at some time afterwards a possible automatic alteration of the infusion.

According to a further preferred embodiment, the control means is adapted so as to adjust the dose of the pharmaceutical substances within predetermined limits according to the kind of therapy, pharmaceutical substance and/or user, which limits are preferably different between local and remote adjustment.

According to a further embodiment there is provided a sensor means adapted to determine therapeutic results or side effects of the therapy due to the infusion of the pharmaceutical substances, wherein the controlling means is adapted to also adjust the dose of the pharmaceutical substances in accordance with the output of the sensor means. For instance, said sensor means may be adapted to record convulsion and/or other measurable parameters of the user's or patient's condition. Moreover, implantation electrodes can be arranged near or on the relevant nerve(s) or epidermally and provided for quantitative controlling of muscle contraction. In particular, side effects can be identified by placing sensors in an implantable catheter tip as used in many chronic diseases in the blood stream (to read states such as temperature, blood pressure, glucose, oxygen and ions) or by the pump asking the user about conditions such as diarrhea, vomiting an nausea.

According to a further preferred embodiment, there is provided a distress feedback modification means adapted to trigger the questions-providing means. In particular, the distress feedback modification means comprises a button and/or a hand set.

Preferably, the questions-providing means is adapted so that the frequency and timing of the questions is associated with the dosing of the pharmaceutical substances on the user's demand. So, the question frequency and their timing can be associated with the pressing of a button (which may be provided as a distress button) or with the operation of a handset for dosing on demand (bolus) by the user or patient, wherein e.g. a record of an initial pain and the pain after a certain time interval is made in order to observe the effect of the additional analgesia according to the dose on demand.

So, the questions may come at predetermined intervals (cf. above mentioned preferred embodiment) and/or when pressing a ("distress") button. Additionally or alternatively, the questions may come at a predetermined time after an extra bolus administration or rate adjustment, and/or by means of an algorithm (preferably consisting of an artificial intelligence algorithm) determining the time after the aforementioned events (provision of the last questions, pressing the button, change of infusion rate or bolus).

According to a further preferred embodiment, there is provided a telecommunication means adapted to provide a communication between parts of the pump infusion system, preferably via a wireless low-power consumption network of a small-range or hard-wired network, and/or between at least one part of said pump infusion system, in particular the pump, and outwards, preferably via a wireless long-distance network. Said telecommunication means may comprise a hand-held communicator which may be provided e.g. with a communication screen where the questions can appear and with a simple button, a button including a circular or linear potentiometer or a touch screen for inputting the answers. In case of a touch screen, a "volume" gradient type graph can be inputted, too. The hand-held communicator is to be used instead of the current conventional bolus button. The hand-held communicator can simultaneously be a long-distance communicator. Preferably, said wireless low-power consumption network has a BLE (Bluetooth Low Energy) or ANT protocol function or any similar function for providing a low-range regional-personal network. In case of a long-distance communicator, communication links using the TCP/IP protocol through WiFi, GSM/GPRS/UMTS, WiMax etc. can be preferably provided.

Preferably, the pump may not be provided with a display, but may comprise just a LED (Light Emitting Diode) indicating a running mode or an alarm mode, or a minimal black/white display due to low battery consumption, whereas the display of mobile phones or other telecommunication means having a larger battery is to be used as a remote display with the benefit of a larger size and color fidelity.

So, since many procedural tasks can be distributed over the whole system, the size of the pump can be made small so that the pump e.g. can be placed at a reservoir of the drug. Further, the pump can be embodied disposable or semidisposable and e.g. supplied in a box with a number of drug reservoirs which are already pre-filled with certain drugs for certain therapies or empty and still to be filled.

Whereas according to the aforementioned embodiment the questions appear on the hand-held communicator and the answers are to be input by the button(s) of the hand-held communicator, according to an alternative preferred embodiment, the pump may comprise a screen on which the questions appear, and buttons, keys or a touch screen for inputting answers.

Preferably, the pump is adapted to control the input and the output, preferably via a display, by means of an internal control process (also called internal state machine) remembering of where you are in the process and navigating through the process according to the answers and the feedback from the user. In other words, the user interface process does not run on an external device (defining a slave of the pump, but comprising no such internal control process), but every single step of communication is carried out by the pump, wherein it is displayed what the pump is doing and driving. For this, a display device can be provided which is connected to the pump trough a wireless local area network (e.g. ANT/BLE protocols) or by a wire, just as in prior art pumps, to display e.g. "write this here". So, in dependence on the use, a rudimentary display may just be needed for palliative care on the one hand, and a large display for hospital use on the other hand, all controlled by the pump. This results in a so-called distributed pump system where it is to be selected which display and associated power consumption is required for the current application. So, the pump which may be considered a medical device has full control of what is displayed and which input is got.

According to a further preferred embodiment, the control means is adapted to adjust the dose of the pharmaceutical substances (1.) by means of a programming to be performed locally or remote by the attending staff, or (2.) by means of a local or remote algorithm of an automatic control wherein the control means preferably includes neural networks and/or a PID (Proportional Integral Differential) algorithm resulting in a closed loop infusion control in both aforementioned cases (1.) and (2.). So, the correction of the parameters of the on-demand dosage and, thus, of the infusion can be done either locally at the pump or via a local connection to a computer, or from remote. The pump can be programmed from the attending staff locally or from remote, or by means of an algorithm of dose correction by using a closed-loop system for providing a feedback. The automatic control system can include neural networks and/or PID algorithms wherein in case of a difference between a desired therapy result and a measured or reported current therapy result a corresponding error is generated by the algorithm. Preferably, for each on-demand dosage the volume of the pharmaceutical substance(s) is algorithmically measured without a simultaneous change of the basal infusion rate. This is very important for multi-drug multi-pump therapies wherein side effects of each drug have to be individually considered and corrected. Should the automatic process correct the pump dosage, if a pharmaceutical company needs to keep the closed loop infusion control algorithm proprietary, the algorithm can be located in a server under its control and output to the pump through telecommunication or telemetry.

According to a further preferred embodiment, there is provided a server means including at least one database for storing data regarding therapy, administration of the pharmaceutical substances, configuration of therapy infusion system user interface for all devices, pharmaceutical substances per therapy, user questions per therapy, protocols and enabling options and limits for remote infusion adjustment per kind of therapy, alarm and alarm enabling configuration, safety check configuration, pharmaceutical substance, preparation prescription, infusion progress and events or actions, and means for transferring at least a part of said data to said control means, preferably along with at least one pass code, barcode, RFID (Radio Frequency IDentification) and/or biometric recognition element. According to a preferred modification of this embodiment, the control means is adapted to allow the local and/or remote programming within predetermined limits according to the kind of therapy, pharmaceutical substance and/or user, which limits are preferably different between local and remote programming.

So, inter alia infusion protocols, events or actions of the pump(s) and sensors, the user's or patient's answers with the time of occurrence, further information of the users, physicians and other attending staff as well as therapies, drugs per therapy, usual and historic protocols per therapy and physician, safety limits for close or local and remote programming per protocol defining the therapy, drug, patient and route of communication can be stored in the database of the server.

Preferably, the questions can be stored initially after having been created, before the questions will be transferred along with infusion parameters to the pump. Then the questions will appear from the pump to the user at the point of care, in particular to any local area network device, and can be changed from remote or locally via the connection with the present computer of the attending staff and a respective local monitoring program.

Whereas in the prior art the protocol library or database is included in the pump, according to a preferred embodiment of the present invention the protocol libraries and databases are included in the server which is remote located and preferably to be accessed via the internet. So, a protocol library and a database can be easily shared between several institutions like e.g. different hospital divisions and home care providers. Moreover, one and the same pump can be used for different treatments by using different protocol libraries or databases. For instance, such a pump can be used for anaesthesia pain control on the one day and for parenteral nutrition on another day by downloading an adequate protocol list from the server means. Further, a notion of patientcentric programming can be introduced: If data regarding drug, concentration etc. are stored in the protocol of the patient database, all what is needed at the pump is to assign a patient by name or e.g. by an RFID or a barcode, and all are downloaded into the pump. Then, a nurse just validates the right protocol, and the rest of the aforementioned safety rights are validated in the same manner so as to start infusion. As an example, the pump can start infusion at a hospital and then stopped, so that all data are transferred to a home care provider who can come with another pump download data and continues infusion at home. Namely, usually a therapy starts in the hospital by using a hospital pump and continues at home by using a pump which is provided from a home care provider. For such a procedure, the relevant data about the infusion and the infusion status like volume infused or to be infused, refractory time for bolus etc. along with the protocol in use and safety options are uploaded from the hospital to the server and downloaded from the server to the pump of the home care provider for continuation of infusion in particular by using the same drug reservoir. So, the present invention allows for a continuation of an elsewhere started infusion.

Preferably, the server can comprise an array of interconnected computers each of which includes the part of the database which is under the competence of the responsible attending staff or office. For instance, the pump and the associated database (including inter alia medical histories and protocols) can be managed and the corresponding data can be stored in a server located with a vendor or sales representative in the respective country, in the users' or patients' databases with their medical histories for a treatment being stored therein, and/or in databases of hospitals and/or home care companies to be accessed by physicians, nurses and other attending staff. Such data are retrieved by a user interface, which is installed in one or more of the server means. Since the communication is carried out between medical devices, the use of the international standard protocol "HL-7" is preferred. Composed are the data for communication with the user by means of known communication techniques, e.g. via webpages, smart phone, tablet personal computer, PDA (Personal Digital Assistant) applications etc., or with the pump. The stages of the therapy, such as prescription, sending to the pharmacy the pharmaceutical substance(s) to be packaged etc., can be part of the pump infusion system or be provided by application of another system with which there is a communication. Respectively, alarms from the pump or occurred during the therapy (in particular through feedback from sensor means) can be forwarded to survival or first aid means provided in the hospital or the home care or rescue company.

Server web pages can be used by the hospital service or a home-care provider and include data about patients treated and nurse personnel organized in groups. So, a nurse who is in charge of a patient will receive via telecommunication a message (in particular an SMS) describing a problem encountered with the pump or the treatment, or be informed that in a given time the drug reservoir must be replaced. From a list of patients, the attending staff can watch the infusion (events and graphs) and therapy progress of each patient in real time over the internet, with alarms popping up in such list.

Further, a patient monitoring service can use and access the database, e.g. via the internet, in order to reveal e.g. the dose infusion history and the answers to the questions. Images, in particular including graphs, can be generated and depicted either locally or at the pump, the hand-held communicator or the large distance communicator or at a local or regional computer or tablet personal computer by using a local connection. In particular, the data of the pump automatically appear on a computer or a tablet personal computer of the physician, nurse and/or other attending staff, which enters the local network connected with the pump infusion system with a password exchange according to the safe network practice, and can be stored on the computer for further processing (e.g. data logging).

Usually, the pump and the other units of the system are permanently connected to the server means so that data are exchanged with the server means regularly online. However, in case the pump is not connected to the server means and a hand-held communicator, e.g. of a nurse, which is connected to the server means online, passes by such a not connected pump, a connection between the pump and said hand-held communicator can be automatically established trough the local wireless network so that data will be immediately exchanged between the pump and the server means via the hand-held communicator. So, pumps which are not online can benefit from the functions as achieved by the present invention, by offline logging into the nurse's hand-held communicator or other mobile device resulting in an automatic download and/or upload of necessary information for the therapy.

The parameters to be altered or corrected during pain treatment are preferably basic infusion rate, volume/weight of dose, time interval between doses, maximum dose per predetermined time interval (e.g. four hours) or maximum number of doses per predetermined time interval (e.g. four hours).

According to a further preferred embodiment, there is provided coding means for coding relevant data and information, in particular about the user, the pump, the pharmaceutical substances and the attending staff, by predetermined codes and/or biometric features, and identification means for identifying said relevant data and information in accordance with use of their code, wherein said control means is adapted to allow an infusion of pharmaceutical substances after acknowledgement of said identification means.

An alteration of the infusion parameters at the pump has been historically carried out in accordance with a nurse and physician pass code, and at predetermined alteration levels which each code allows for. However, a remote alteration of infusion parameters results in a complicated safety problem, because conventional computers and communication means and paths are not checked for safe medical use.

According to a still further preferred embodiment, security is ensured with the ascertainment of both the digital signatures of the participants of the communication who usually are patients on the one hand and physicians or nurses on the other hand, as well as by using a full cycle of information. The digital signatures can be passwords, output signals from RFID tags, barcodes or output signals from biometric features or elements whose imprint of the index finger or eye picture is already on the market. Preferably, an RFID is provided on a drug reservoir behind a label which partially or completely indicates data like therapy, patient, pharmaceutical substance used, infusion parameters and infusion limits, while the same data are also stored in the RFID. The reading-out from the system or from an accessory of the nurse, the transfers to the pump and the system and also the identification is carried out, if it is the right patient who receives the correct medication for the correct disease within the limits allowed, and following the identification the pump is possibly programmed accordingly, and the infusion to the patient is allowed. The mentioned accessory of the nurse can be a tablet personal computer or an RFID reader which can be automatically or manually connected to the local network of the pump infusion system.

According to a second aspect of the present invention there is provided a method for remote programming a pump infusion system, said pump infusion system comprising a pump adapted to be attached to a user and to cause infusion of pharmaceutical substances into the user's body, preferably according to at least any one of the preceding claims, characterized by the steps of assigning to a predetermined program, comparing a protocol to be programmed with a protocol coming from said pump, eliminating possible errors of non-medically certified intervening devices and means, and executing programming.

In particular, when long distance communication means are used, for or during remote programming the same type of programming as it comes from the pump will appear. If no difference between the current programming and the programming as it comes from the pump is to be observed, this means that insecure communication means inbetween has not affected the data and hence the pump comprises a correct programming. So, according to the present invention all relevant information are received and transmitted back integrally and not piece per piece. Therefore, the present invention is advantageous for web remote programming by taking into consideration that it would take too long to receive and transmit back a single character, character by character. In case of the provision of a keyboard and a display or equivalently a touch screen, at the point of care close to the user or patient, the keyboard input is transferred to the pump, and according to an internal control process running in the user interface the pump sends the keyboard input back to the display so that it is sure which input the pump has got (feedback). By doing so, the safety of the system is guaranteed whatever an unsafely operating system is used. This has been a big problem by many medical companies which need support by an external device like e.g. a tablet personal computer, but cannot use it because any application running on such devices is not considered "medically safe". This problem is overcome due to the present invention by giving full control of the user interface process to the "medically safe" pump, wherein it is a key element of the keyboard which controls the communication here.

According to a third aspect of the present invention, there is provided a method for remote programming a pump infusion system, said pump infusion system comprising a pump adapted to be attached to a user and to cause infusion of pharmaceutical substances into the user's body, preferably according to at least any one of the preceding claims, characterized by the steps of sending infusion parameters from a user interface to a server means, storing them in a database in the server means, and also buffering them in the user interface, retrieving said infusion parameters from the database of the server means and sending them back to the user interface, in the user interface, comparing the infusion parameters buffered therein with the infusion parameters sent back from the server means in order to verify whether or not an error has occurred during the transmission process, and, if it is found that no error has occurred during the transmission process, sending a "user validation" message from the user interface to the server means, and upon receipt of the "user validation" message at the server means, transferring the infusion parameters from the server means to the pump.

Preferably, the above method is characterized by the further steps of sending the infusion parameters from the pump back to the server means, in the server means, comparing the infusion parameters stored therein with the infusion parameters sent back from the pump in order to verify whether or not an error has occurred during the transmission process, and, if it is found that no error has occurred during the process, sending an acknowledgement from the server means to the pump, and transmitting a programming execution command from the server means to the pump, and programming the pump by using the infusion parameters.

According to a fourth aspect of the present invention, there is provided a method for remote programming a pump infusion system, said pump infusion system comprising a pump adapted to be attached to a user and to cause infusion of pharmaceutical substances into the user's body, preferably according to at least any one of the preceding claims, characterized by the steps of sending infusion parameters from a user interface to a server means, storing them in a database in the server means, and also buffering said infusion parameters in the user interface, retrieving said infusion parameters from the database of the server means and sending them to the pump, sending said infusion parameters from the pump back to the server means, and in the server means, comparing the infusion parameters stored therein with the infusion parameters sent back from the pump in order to verify whether or not an error has occurred during the transmission process, and, if it is found that no error has occurred during the process, sending an acknowledgement from the server means to the pump.

Preferably, the above method is characterized by the further steps of sending the infusion parameters from the server means also back to the user interface, in the user interface, comparing the infusion parameters buffered therein with the infusion parameters sent back from the server means in order to verify whether or not an error has occurred during the transmission process, and, if it is found that no error has occurred during the process, transmitting a "user validation" message from the user interface to the server means, and transmitting a programming execution command from the server means to the pump, and programming the pump by using the infusion parameters.

The user interface may be implemented as a hardware and/or software component basically in any unit of the system which is operated by a user. In particular, the pump is provided with such a user interface. Preferably, the user interface consists of a visual program running on a display of the aforementioned unit(s).

A characteristic of communication according to the present invention is the provision of a very small amount of information to be transferred, wherein a multiple transmission is preferred for security reasons.

The aforementioned methods are particularly advantageous for long distance communication in order to achieve the required safety. Since in a long distance communication informations sent and got back are subject to some delay and interference, according to the aforementioned second to fourth aspects of the present invention a comparison is carried out between what is sent from the user to the pump and what is received from the pump at the user.

Due to the present invention, there are provided validating procedures which a critical device as the pump in question here needs to rely on so as to be able to safely operate in a not reliable environment. Preferably, five safety rights comprising patient validation, drug validation, pump validation, nurse validation and doctor validation are checked by a communicating part (in particular WiFi and GSM) of the pump, to enable infusion if these rights are validated. If not, the attending staff, in particular a nurse, or the patient are asked for pending validations preferably by a computer, a phone application or the pump itself.

Preferably, the user's or patient's safety is increased by limiting the range or amount of alteration of the initial parameters so as to allow the pump to be additionally programmed within limits only. These limits are initially provided by the pump and transferred to the server and from the server to the user interface, so that the user is prevented from programming outside the limits. These limits can include lower limits above which the programmer is informed in order to avoid errors. Further, the limits can be extended in therapies such as regional analgesia, where the risk is lower, or narrowed in case of intravenous or epidural analgesia or other diseases where the risk is greater. These limits can be set up by the pump if it is programmed preferably by a so-called "therapy" menu, or by a physician (using a maximum permissions programming code) if the pump does not have any programming regarding therapy and/or drug. So, due to these safety limits implemented in the pump, the infusion is limited in case of an internet malfunction, wherein these limits are different for different therapies, drugs and/or patients. The responsible attending staff (physicians or nurses) has to validate on the pump the limits received from the server, before remote programming is allowed. Accordingly, a risk analysis can be used as a tool for certification of the pump in order to allow a process to be used depending on the risk for the patient. When the risk is analyzed, it is estimated whether or not a process fails in particular due to a wrong drug dose administration. For not dangerous drugs or pharmaceutical substances, a user validation is not needed. For less dangerous drugs, a user validation at a lower level may be used which gives an indication to the doctor that there is no need to wait much for a comparative result to appear. For more dangerous drugs, a user validation at a higher level should be used which gives an indication to the doctor to wait for the comparative result to appear. Safety, of course, is further guaranteed by limits as mentioned above.

So, the pump according to the present invention can be preferably provided with the ability to let the attending staff, the automatic pump process or the distant server means change certain infusion parameters within a predefined limit. These parameters can also be changed by the physician over the internet by using a safe telecommunication or telemetry process as discussed above. The method used by medical personnel is the automatic process of 'trimming within limits' preset by the physician. The pump can be able to observe these limits so as to prevent excessive over- or under-infusion.

The aforementioned database on the server including data regarding therapies, drugs per therapy, protocols and safety limits of local and remote programming per therapy/drug/type of patient can be, preferably gradually, downloaded from the server to the pump for manageability purposes, preferably with fewer choices, as many as the use of the pump requires, and for the maintenance of a database updated with the latest data.

In the following, a preferred embodiment of the present invention will be described with reference to the accompanying figures, in which.

Figure 1:
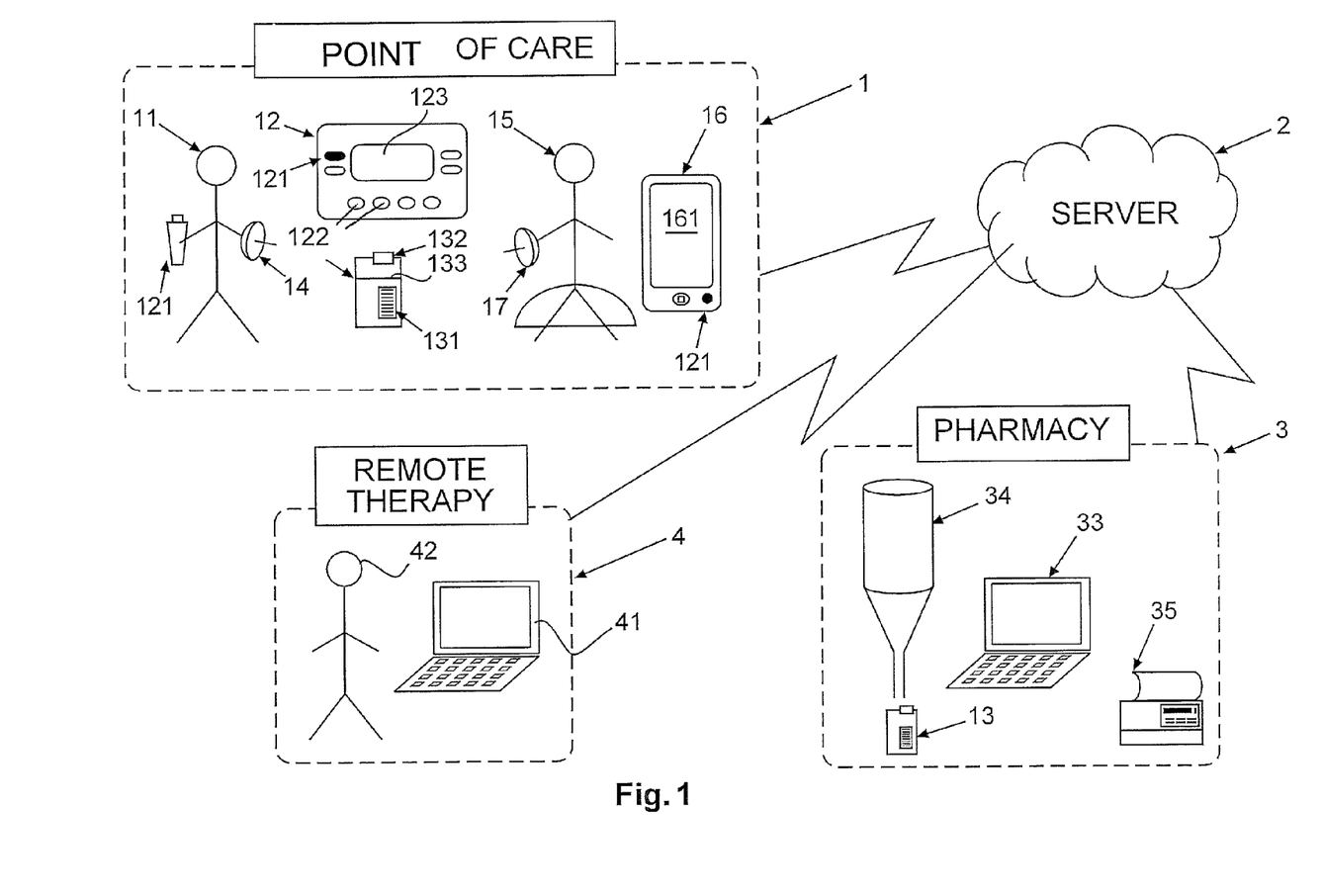
FIG. 1 schematically shows a block diagram depiction of a pump infusion system according to a preferred embodiment of the present invention.

A pump infusion system according to a preferred embodiment of the present invention is schematically shown as a block diagram depiction in FIG. 1.

At a point of care 1 schematically shown are a patient 11 who can also be called a user, a pump 12, a drug bag 13, a nurse 15 and a communication device 16.

In the example shown, the patient 11 is provided with a RFID tag 14 which is attached to her/his body and preferably to her/his arm or finger as indicated in FIG. 1. Alternatively or additionally the patient 11 can also be provided with a "bolus" or "distress" button 121 which is attached to her/his body and preferably to her/his arm or finger as indicated in FIG. 1, too.

In the shown embodiment, the pump 12 is configured as a so-called minimal pump comprising all those features which are necessary for working as a pump and controlling the pumping function. So, the pump 12 includes a control means for controlling the pumping function so as to adjust the dose of drug(s) or pharmaceutical substance(s) to be fed into the body of the patient 11 to which the pump 12 is to be attached. Further, the pump 12 includes questions-providing means for providing questions regarding the effects of administration of the drug(s), and recording means for recording answers to said questions. As schematically shown in FIG. 1, the pump 12 is further provided with a "bolus" or "distress" button 121 and some further buttons 122 which are used for inputting answers to the questions after having been created by the questions-providing means. In the shown embodiment, the pump 12 further comprises a simple display screen 123 for displaying the questions as created by the questions-providing means, the input answers and further data and messages. Moreover, the pump 12 includes wired or wireless bi-directional telecommunication means for being connected to other units and devices of the system.

In the shown embodiment, the drug bag 13 is provided with a label 131 preferably comprising a barcode and an RFID tag 132 and is filled with a drug or pharmaceutical substance 133. The drug bag 13 is coupled via a tube or hose (not shown) to the pump 12 so as to supply the pump 12 with a drug. Like the pump 12, the drug bag 13 is also adapted to be attached to the body of the patient 11. Instead of being directly attached to the body of the patient 11, the pump 12 can alternatively be adapted to be attached to the drug bag 13, or according to a further preferred embodiment the pump 12 and the drug bag 13 can define a common unit to be attached to the body of the patient 11.

In the shown example, the nurse 15 is provided with a tag 17, too, which is preferably attached to her hand or finger as schematically shown in FIG. 1.

The hand-held communicator 16 comprises a "bolus" or "distress" button 121, a large display screen 161 and can be embodied as a PDA (Personal Digital Assistant), a smart phone or a tablet personal computer having a telecommunication function. The telecommunication function comprises a short-range as well as a long-distance communication ability. So, according to the described embodiment the hand-held communicator 16 includes a local area network interface for a wireless connection with a pump 12 via a local area network; however, rather than a wireless communication a wired connection between the pump 12 and the hand-held communicator can be alternatively provided. Moreover, the hand-held communicator 16 includes a long range network interface as well so as to communicate with external remote devices.

Remote from the point of care 1 is provided a server 2 which communicates with the point of care 1 via the internet. The server 2 includes at least one database for storing several data which are relevant for the infusion process.

Reference numeral "3" denotes a pharmacy which is schematically shown as a block in FIG. 1 and comprises inter alia a computer 33, a drug filling equipment 34 and a combined barcode label printer and RFID programmer 35 for printing out barcode labels and programming the RFID tag 132. The computer 33 includes a telecommunication interface for connection with the server 2 via the internet. The drug filling equipment 34 and the combined barcode label printer and RFID programmer 35 are coupled to the computer 33 which is not shown in FIG. 1. The drug filling equipment 34 is provided for filling a drug bag 13 as schematically indicated in FIG. 1.

As further shown in FIG. 1, the server 2, is also connected via the internet to a point of remote therapy 4 where a computer 41 is located which is operated by a physician or doctor 42. The computer 41 also comprises a telecommunication interface for the connection with the server 2.

Further, in any unit of the system which unit is operated by a user, a user interface may be implemented as a hardware and/or software component. Preferably, the user interface consists of a visual program running on a display of such unit(s). In the embodiment according to FIG. 1, the pump 12, the hand-held communicator 16 and the computers 33 and 41 include such user interface as a visual program running on their display.

At predetermined time intervals which can be programmable, a series of questions is provided by the questions-providing means in the pump 12 which questions describe quantitatively and qualitatively the condition of mobility, pain etc. According to the kind of list or table of questions appearing, the user or patient may answer either "yes" or "no" or with a quantitative reference, e.g. by selection from a list of prescribed types of answers given as e.g. "bad"-"good"-"better"-"excellent" or numbers from "1" to "10". A preferred implementation of the questions which may be different per used therapy and/or selected pharmaceutical substance or drug and of the kind of the corresponding answers is as follows:

| QUESTION | ANSWER |
| --- | --- |
| Pain via still | 0 to 10 |
| Pain during emotion | 0 to 10 |
| Extreme numbing | yes/no |
| Blockage of movement | yes/no |
| Difficulty in walking | 0 to 10 |
| Activity | 0 to 10 |
| Insomnia | 0 to 10 |
| Puffing of legations | yes/no |
| Satisfaction | 0 to 10 |
| Service assessment | 0 to 10 |
| Nausea | yes/moderate/no |
| Vomiting | yes/trend/no |
| Diarrhea | yes/slight/no |

The control means of the pump 12 is adapted so as to adjust the dose of the pharmaceutical substances within predetermined limits according to the kind of therapy, pharmaceutical substance and/or user, which limits are preferably different between local and remote adjustment.

Additionally, sensors (not shown) can be attached to the body of the patient 11 which sensors are adapted to determine therapeutic results or side effects of the therapy due to the infusion of the pharmaceutical substances, wherein the controlling means is adapted to also adjust the dose of the pharmaceutical substances in accordance with the output of the sensor means. For instance, said sensors may be adapted to record convulsion and/or other measurable parameters of the user's or patient's condition. Moreover, implantation electrodes can be arranged near or on the relevant nerve(s) or epidermally and provided for quantitative controlling of muscle contraction. In particular, side effects can be identified by placing sensors in an implantable catheter tip as used in many chronic diseases in the blood stream (to read states such as temperature, blood pressure, glucose, oxygen and ions) or by the pump asking the user about conditions such as diarrhea, vomiting and nausea.

The questions-providing means is adapted so that the frequency and timing of the questions is associated with the dosing of the pharmaceutical substances on the user's demand. So, the question frequency and their timing can be associated with the pressing of the button 121 at the pump 12 which button is provided as a distress button or dosing on demand (bolus) from the user or patient, wherein e.g. a record of an initial pain and the pain after a certain time interval is made in order to observe the effect of the additional analgesia according to the dose on demand.

So, the questions come at predetermined intervals (cf. above mentioned preferred embodiment) and/or when pressing a ("distress") button. Additionally or alternatively, the questions may come at a predetermined time after an extra bolus administration or rate adjustment, and/or by means of an algorithm (preferably consisting of an artificial intelligence algorithm) determining the time after the aforementioned events (provision of the last questions, pressing the button, change of infusion rate or bolus).

The telecommunication means in the pump 12 and the hand-held communicator 16 provide a communication between parts of the pump infusion system at the point of care 1 via a wireless low-power consumption network of a small-range or hard-wired network, and between the point of care 1, the server 2, the pharmacy 3 and the point of remote therapy 4 via a wireless long-distance network. The hand-held communicator 16 is provided e.g. with a communication screen 161 where the questions can appear and with a simple button, a button including a circular or linear potentiometer or a touch screen for inputting the answers. In case of a touch screen, a "volume" gradient type graph can be inputted, too. The hand-held communicator 16 is to be used instead of the current conventional bolus button. The hand-held communicator 16 can simultaneously be a long-distance communicator. Preferably, the wireless low-power consumption network has a BLE (Bluetooth Low Energy) function or any similar function for providing a low-range regional-personal network. In case of a long-distance communicator, communication links using the TCP/IP protocol through WiFi, GSM/GPRS/UMTS, WiMax etc. are preferably provided.

Alternatively, the pump may not be provided with a display, but may comprise just a LED (Light Emitting Diode) indicating a running mode or an alarm mode, or a minimal black/white display due to low battery consumption, whereas the display of mobile phones or other telecommunication means having a larger battery is to be used as a remote display with the benefit of a larger size and color fidelity.

Preferably, the control means of the pump 12 is adapted to adjust the dose of the drug 133 (1.) by means of a programming to be performed locally or remote by the attending staff, or (2.) by means of a local or remote algorithm of an automatic control wherein the control means preferably includes neural networks and/or a PID (Proportional Integral Differential) algorithm resulting in a closed loop infusion control in both aforementioned cases (1.) and (2.). So, the correction of the parameters of the on-demand dosage and, thus, of the infusion can be done either locally at the pump 12 or via a local connection to the hand-held communicator 16, or from remote. The pump 12 is programmed from the attending staff locally or from remote, or by means of an algorithm of dose correction by using a closed-loop system for providing a feedback. The automatic control system can include neural networks and/or PID algorithms wherein in case of a difference between a desired therapy result and a measured or reported current therapy result a corresponding error is generated by the algorithm. Preferably, for each on-demand dosage the volume of the pharmaceutical substance(s) is algorithmically measured without a simultaneous change of the basal infusion rate. Should the automatic process correct the pump dosage, if a pharmaceutical company needs to keep the closed loop infusion control algorithm proprietary, the algorithm can be located in a server under its control and output to the pump through telecommunication or telemetry.

The server 2 includes at least one database for storing data regarding therapy, administration of the pharmaceutical substances, configuration of therapy infusion system user interface for all devices, pharmaceutical substances per therapy, user questions per therapy, protocols and enabling options and limits for remote infusion adjustment per kind of therapy, alarm and alarm enabling configuration, safety check configuration, pharmaceutical substance, preparation description, infusion progress and events or actions, and means for transferring at least a part of said data to said control means, preferably along with at least one pass code, barcode, RFID and/or biometric recognition element. Preferably, the control means is adapted to allow the local and/or remote programming within predetermined limits according to the kind of therapy, drug 133 and/or user, which limits are preferably different between local and remote programming.

So, inter alia infusion protocols, events or actions of the pump(s) and sensors, the user's or patient's answers with the time of occurrence, further information of the users, physicians and other attending staff as well as therapies, drugs per therapy, usual and historic protocols per therapy and physician, safety limits for close or local and remote programming per protocol defining the therapy, drug, patient and route of communication can be stored in the database of the server.

The questions are initially stored in the server 2 after having been created, before the questions will be transferred along with infusion parameters to the pump 12. Then the questions will appear from the pump 12 to the user at the point of care 1, in particular to any local area network device, and can be changed from remote or locally via the connection with the present computer of the attending staff and a respective local monitoring program.

Protocol libraries and databases are included in the server 2 which is remote located and to be accessed via the internet. So, a protocol library and a database can be easily shared between several institutions like e.g. different hospital divisions and home care providers. Moreover, one and the same pump can be used for different treatments by using different protocol libraries or databases. For instance, such a pump can be used for anaesthesia pain control on the one day and for parenteral nutrition on another day by downloading an adequate protocol list from the server 2. Further, a notion of patient centric programming can be introduced: If data regarding drug 133, concentration etc. are stored in the protocol of the patient database, all what is needed at the pump 12 is to assign a patient by name or e.g. by an RFID or a barcode, and all are downloaded into the pump. Then, a nurse 15 just validates the right protocol, and the rest of the aforementioned safety rights are validated in the same manner so as to start infusion. As an example, the pump 12 can start infusion at a hospital and then stopped, so that all data are transferred to a home care provider who can come with another pump download data and continues infusion at home. Namely, usually a therapy starts in the hospital by using a hospital pump and continues at home by using a pump which is provided from a home care provider. For such a procedure, the relevant data about the infusion and the infusion status like volume infused or to be infused, refractory time for bolus etc. along with the protocol in use and safety options are uploaded from the hospital to the server 2 and downloaded from the server 2 to the pump of the home care provider for continuation of infusion in particular by using the same drug bag 13.

Preferably, the server 2 can comprise an array of interconnected computers (not shown) each of which includes the part of the database which is under the competence of the responsible attending staff or office. For instance, the pump 12 and the associated database (including inter alia medical histories and protocols) can be managed and the corresponding data can be stored in a server 2 located with a vendor or sales representative in the respective country, in the patients' databases with their medical histories for a treatment being stored therein, and/or in databases of hospitals and/or home care companies to be accessed by physicians, nurses and other attending staff. Such data are retrieved by a user interface, which is installed in the server 2. Since the communication is carried out between medical devices, the use of the international standard protocol "HL-7" is preferred. Composed are the data for communication with the patient 11 by means of known communication techniques, e.g. via webpages, smart phone, tablet personal computer, PDA (Personal Digital Assistant) applications etc., or with the pump 12. The stages of the therapy, such as prescription, sending to the pharmacy the pharmaceutical substance(s) to be packaged etc., can be part of the pump infusion system or be provided by application of another system with which there is a communication. Respectively, alarms from the pump 12 or occurred during the therapy (in particular through feedback from the sensor 2) can be forwarded to survival or first aid means provided in the hospital or the home care or rescue company (not shown).

Server web pages can be used by the hospital service or a home-care provider and include data about patients treated and nurse personnel organized in groups. So, the nurse 15 who is in charge of the patient 11 will receive via telecommunication a message (in particular an SMS) describing a problem encountered with the pump 12 or the treatment, or be informed that in a given time the drug reservoir must be replaced. From a list of patients, the attending staff can watch the infusion (events and graphs) and therapy progress of each patient in real time over the internet, with alarms popping up in such list.

Further, a patient monitoring service (not shown) can use and access the database, e.g. via the internet, in order to reveal e.g. the dose infusion history and the answers to the questions. Images, in particular including graphs, can be generated and depicted either locally or at the pump 12, the hand-held communicator 16 or the large distance communicator or at a local or regional computer or tablet personal computer by using a local connection. In particular, the data of the pump 12 automatically appear on a computer or a tablet personal computer of the physician, nurse and/or other attending staff, which enters the local network connected with the pump infusion system with a password exchange according to the safe network practice, and can be stored on the computer for further processing (e.g. data logging). In case the pump 12 is not connected to the server 2 and a hand-held communicator 16 of a nurse 15, which is connected to the server 2 online, passes by the not connected pump 12, a connection between the pump 12 and the hand-held communicator 16 can be automatically established through the local wireless network so that data will be immediately exchanged between the pump 12 and the server 2 via the hand-held communicator 16.

The parameters to be altered or corrected during pain treatment are preferably basic infusion rate, volume/weight of dose, time interval between doses, maximum dose per predetermined time interval (e.g. four hours) or maximum number of doses per predetermined time interval (e.g. four hours).

Security is ensured with the ascertainment of both the digital signatures of the participants of the communication who usually are patients on the one hand and physicians or nurses on the other hand, as well as by using a full cycle of information. In the embodiment shown in FIG. 1, the digital signatures are included in the output signals from the tags which preferably consist of RFID tags 14, 17 and 132 shown in FIG. 1. As already mentioned above, one of these tags, i.e. the tag 132 is provided on the drug bag 13 adjacent to label 131 which partially or completely indicates data like therapy, patient, pharmaceutical substance used, infusion parameters and infusion limits, while the same data are also stored in the RFID. The reading-out from the system or from an accessory of the nurse 15, the transfers to the pump 12 and the system and also the identification is carried out, if it is the right patient 11 who receives the correct medication and infusion protocol regarding the correct disease within the limits allowed, and the correct administration route, and following the identification the pump 12 is possibly programmed accordingly, and the infusion to the patient 11 is allowed. The mentioned accessory of the nurse 15 can be a tablet personal computer or an RFID reader which can be automatically or manually connected to the local network of the pump infusion system.

During the therapy or infusion, by pressing the distress button 121 or arising a sensor alarm, questions are sent to the patient and then the answers are received, and according to said answers a correction of the infusion is carried out by means of an automatic control or by a remote action of the physician 42 at the point of remote therapy 4. Following a successful identification of the physician 42, a safe remote programming is carried out within limits, so that in such a case the physician 42 also works as a programmer.

Figure 2:
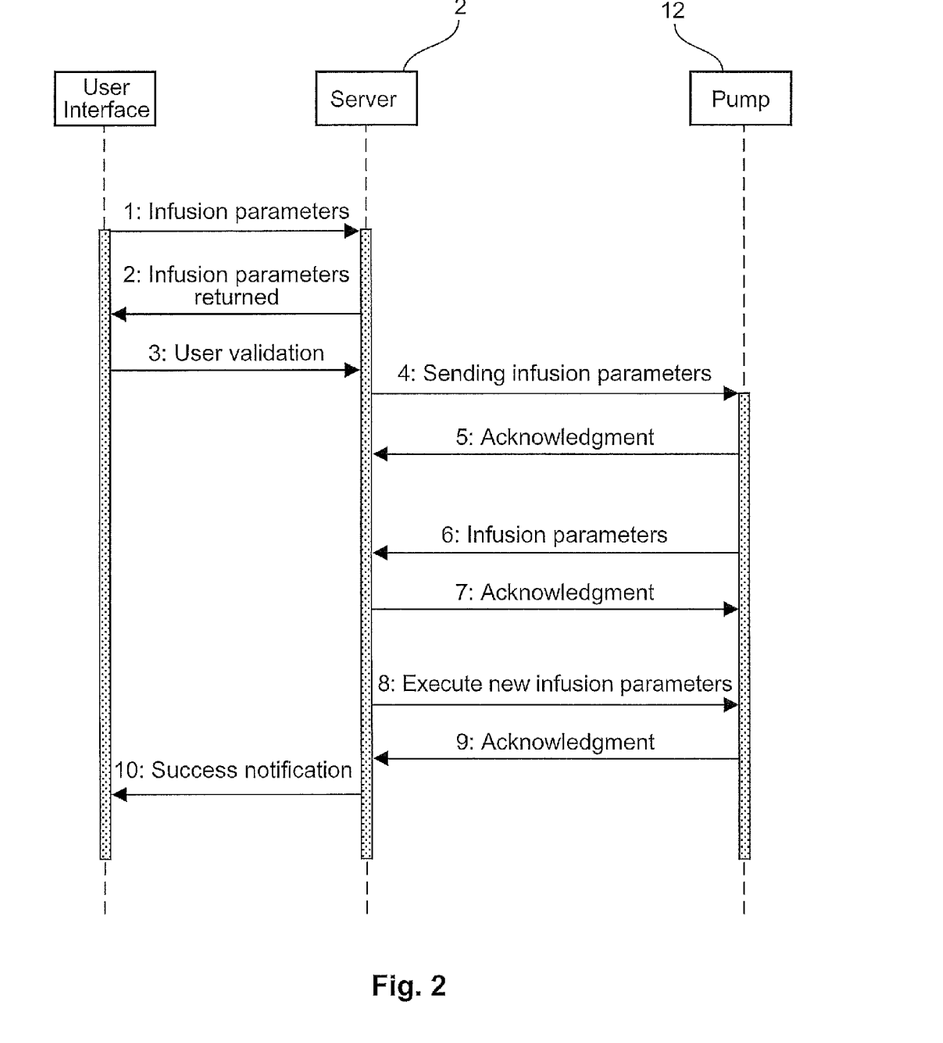
FIG. 2 shows a method of safe remote programming according to a first preferred implementation of the present invention.

FIG. 2 shows a method of a safe remote programming according to a first preferred implementation which includes the following stages:

1. The user interface sends infusion parameters to the server which stores them in a database, wherein said infusion parameters are also buffered in the user interface.
2. The server retrieves said infusion parameters from its database and sends them back to the user interface.
3. In the user interface the infusion parameters buffered therein are compared with the infusion parameters sent back from the server in order to verify whether or not an error has occurred during the transmission process, and, if it is found that no error has occurred during the transmission process, the user interface sends a "user validation" message to the server.
4. Upon receipt of said "user validation" message from the user interface, the server transfers the infusion parameters to the pump.
5. The pump acknowledges receipt of the infusion parameters to the server.
6. The pump sends the infusion parameters back to the server.
7. In the server the infusion parameters stored therein are compared with the infusion parameters sent back from the pump in order to verify whether or not an error has occurred during the transmission process, and, if it is found that no error has occurred during the process, the server sends an acknowledgment to the pump.
8. The server transmits a programming execution command to the pump so that the pump is programmed by using the infusion parameters.
9. Following a successful programming the pump sends an acknowledgement to the server.
10. The server informs the user interface of the successful remote programming.

Figure 3:
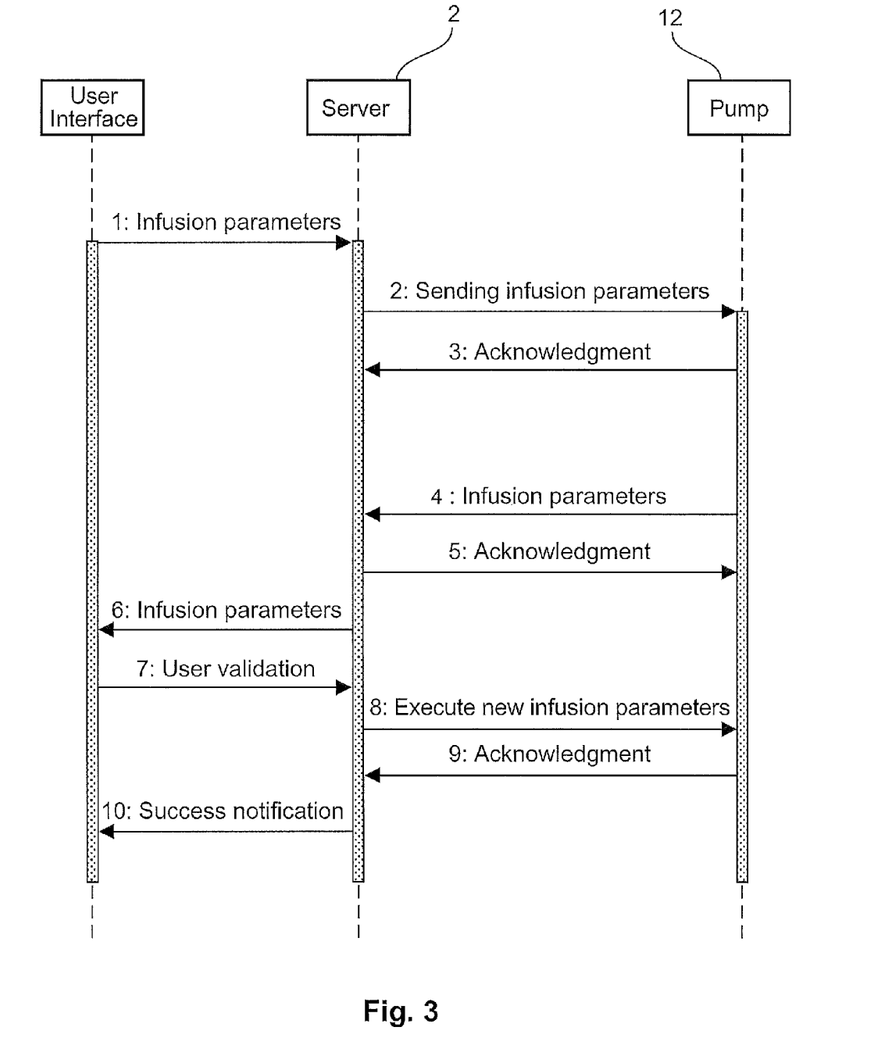
FIG. 3 shows a method of safe remote programming according to a second preferred implementation of the present invention.

FIG. 3 shows a method of a safe remote programming according to another preferred implementation which includes the following stages:

1. The user interface sends infusion parameters to the server which stores them in the database, wherein said infusion parameters are also buffered in the user interface.
2. The server retrieves said infusion parameters and sends them to the pump.
3. The pump acknowledges receipt of the infusion parameters.
4. The pump sends the infusion parameters back to the server.
5. In the server, the stored infusion parameters are compared with the infusion parameters sent back from the pump in order to verify whether or not an error has occurred during the transmission process, and, if it is found that no error has occurred during the process, the server sends an acknowledgment to the pump.
6. The server also sends the infusion parameters back to the user interface.
7. In the user interface, the infusion parameters buffered therein are compared with the infusion parameters sent back from the server in order to verify whether or not an error has occurred during the transmission process, and, if it is found that no error has occurred during the process, the user interface transmits a "user validation" message to the server.
8. The server transmits a programming execution command to the pump so that the pump is programmed by using the infusion parameters.
9. Following a successful programming, the pump sends an acknowledgement to the server.
10. The server informs the user interface of the successful programming.

Preferably, the user's or patient's safety is increased by limiting the range or amount of alteration of the initial parameters so as to allow the pump 12 to be additionally programmed within limits only. These limits are initially provided by the pump 12 and transferred to the server 2 and from the server 2 to the user interface, so that the patient 11 is prevented from programming outside the limits. These limits include lower limits above which the programmer is informed in order to avoid errors. Further, the limits can be extended in therapies such as regional analgesia, where the risk is lower, or narrowed in case of intravenous or epidural analgesia or other diseases where the risk is greater. These limits can be set up by the pump if it is programmed preferably by a so-called "therapy" menu, or by a physician (using a maximum permissions programming code) if the pump 12 does not have any programming regarding therapy and/or drug 133. So, due to these safety limits implemented in the pump, the infusion is limited in case of an internet malfunction, wherein these limits are different for different therapies, drugs and/or patients. The responsible attending staff (physicians or nurses) has to validate on the pump 12 the limits received from the server 2, before remote programming is allowed. The initial therapy protocol and the limits for the therapy, i.e. the limits of alterations permitted by the protocol, can be programmed by any means, e.g. manually at the pump 12, at the hand-held communicator 16 or by downloading through the internet, wherein validation of the attending staff on the display screen 123 of the pump 12 or on the display screen 161 of the hand-held communicator 16 controlled by the pump 12 is required through the aforementioned safe process. The remote programming, in particular for correction of the current therapy, which e.g. is carried out by the physician 42 on the computer 41 at the point of remote therapy 4, is allowed with the aforementioned process only within the validated limits.

So, the pump 12 is preferably provided with the ability to let the attending staff, the automatic pump process or the distant server 2 change certain infusion parameters within a predefined limit. These parameters can also be changed by the physician over the internet by using a safe telecommunication or telemetry process as discussed above. The method used by medical personnel is the automatic process of 'trimming within limits' preset by the physician. The pump 12 is able to observe these limits so as to prevent excessive over- or under-infusion.

The data regarding therapies, drugs per therapy, protocols and safety limits of local and remote programming per therapy/drug/type of patient can be, preferably gradually, downloaded from the server 2 to the pump 12 for manageability purposes, preferably with fewer choices, as many as the use of the pump requires, and for the maintenance of a database updated with the latest data.

Finally, it should be noted that the above described embodiment is of an example for implementing the present invention. However, the scope of the present invention should not necessarily be limited by the above description, but is defined by the following claims.

The invention claimed is:
1. Pump infusion system, comprising
at least a pump adapted to be attached to a user and to cause infusion of pharmaceutical substances into the user's body,
data processing means for showing or editing information on activity of the pump, remote programming means for defining operating limits of the pump per therapy and user, ID tags, questions providing means for providing questions regarding the effects of administration of the pharmaceutical substances, transmitting means for transmitting answers to said questions to an attending staff, recording means for recording said answers, and control means for controlling said pump so as to adjust the dose of the pharmaceutical substances in accordance with at least one of said answers within the operating limits of the pump.

2. Pump infusion system according to claim 1, characterized in that said questions-providing means is adapted to provide questions in predetermined or algorithmically calculated time intervals.

3. Pump infusion system according to claim 1 characterized by sensor means adapted to determine therapeutic results or side effects of the therapy due to the infusion of the pharmaceutical substances, wherein said controlling means is adapted to also adjust the dose of the pharmaceutical substances in accordance with the output of said sensor means.

4. Pump infusion system according to claim 1, characterized by a distress feedback modification means adapted to trigger said questions-providing means.

5. Pump infusion system according to claim 1, characterized in that said questions-providing means is adapted so that the frequency and timing of the questions is associated with the dosing of the pharmaceutical substances on the user's demand.

6. Pump infusion system according to claim 1, characterized by a telecommunication means adapted to provide a communication between parts of said pump infusion system, and/or between at least one part of said pump infusion system, in particular the pump, and outwards.

7. Pump infusion system according to claim 1 characterized in that said control means is adapted so as to adjust the dose of the pharmaceutical substances within predetermined limits according to the kind of therapy, pharmaceutical substance and/or user.

8. Pump infusion system according to claim 1, characterized by coding means for coding relevant data and information, in particular about the user, the pump, the pharmaceutical substances and the attending staff, by predetermined codes and/or biometric features, and identification means for identifying said relevant data and information in accordance with use of their code, wherein said control means is adapted to allow an infusion of pharmaceutical substances after acknowledgement of said identification means.

9. Pump infusion system according to claim 1, wherein said ID tags are adapted to define therapy and user so that the operating limits apply to said therapy and said user.

10. Pump infusion system according to claim 1, further comprising
 a server for translating a doctor's prescription to therapy management operations and a protocol assigned to a specific user, and
 means for therapy remote monitoring by the attending staff using system devices during more than one infusion, observing therapy feedback answers and measurements specific for the therapy, while protocol and therapy corrections are done from said system devices accordingly based on the feedback.

11. Pump infusion system according to claim 1, wherein said ID tags, are adapted to identify the user, and further means are provided to download from a server a protocol which is linked to a specific user, in a user driven pump programming mode, thus avoiding programming errors while programming.

12. Pump infusion system according to claim 1, further comprising means adapted to assign a drug preparation and a packaging means to an ID for a specific prescription and to transmit them for identification at use.

13. Pump infusion system according to claim 1, further comprising means to make available the attending staff all safety rights for validation on the pump so as to start an infusion according to a determined protocol.

14. Pump infusion system according to claim 1, characterized in that said control means is adapted to adjust the dose of the pharmaceutical substances by means of a programming to be performed locally or remote by the attending staff, or by means of a local or remote algorithm of an automatic control.

15. Pump infusion system according to claim 14, characterized in that said control means adjusts the dose of the pharmaceutical substances by means of a programming to be performed remote by the attending staff.

16. Pump infusion system according to claim 1, characterized by server means including at least one database for storing data regarding therapy, administration of the pharmaceutical substances, configuration of therapy infusion system user interfaces for all devices, pharmaceutical substances per therapy, user questions per therapy, protocols and enabling options and limits for remote infusion adjustment per kind of therapy, alarm and alarm enabling configuration, safety check configuration, pharmaceutical substance preparation prescription, infusion progress and events or actions, and means for transferring at least a part of said data to said control means.

17. Pump infusion system according to claim 16, characterized in that said control means is adapted to allow the local and/or remote programming within predetermined limits according to the kind of therapy, pharmaceutical substance and/or user.

* * * * *